US012626406B2

US 12,626,406 B2

(12) United States Patent
Huang et al.

(10) Patent No.: US 12,626,406 B2
(45) Date of Patent: May 12, 2026

(54) TAG-GUIDED IMAGE POSITIONING METHOD AND SYSTEM

(71) Applicant: NATIONAL TSING HUA UNIVERSITY, Hsinchu (TW)

(72) Inventors: Wei-Lun Huang, Hsinchu (TW); Yung-Shin Tseng, Hsinchu (TW); Wei-Lin Chen, Hsinchu (TW); Hui-Yu Tsai, Hsinchu (TW)

(73) Assignee: NATIONAL TSING HUA UNIVERSITY, Hsinchu (TW)

( * ) Notice: Subject to any disclaimer, the term of this patent is extended or adjusted under 35 U.S.C. 154(b) by 207 days.

(21) Appl. No.: 18/512,902

(22) Filed: Nov. 17, 2023

(65) Prior Publication Data

US 2025/0069265 A1      Feb. 27, 2025

(30) Foreign Application Priority Data

Aug. 24, 2023     (TW) .................................. 112131972

(51) Int. Cl.
*G06T 7/80*          (2017.01)
*G06V 20/50*        (2022.01)
*G16H 40/67*        (2018.01)

(52) U.S. Cl.
CPC ................ *G06T 7/80* (2017.01); *G06V 20/50* (2022.01); *G16H 40/67* (2018.01);
(Continued)

(58) Field of Classification Search
CPC ....... G06T 2200/24; G06T 2207/30004; G06T 2207/30204; G06T 7/80; G16H 40/67; G06V 20/50; G06V 2201/03
See application file for complete search history.

(56) References Cited

U.S. PATENT DOCUMENTS

2021/0353486 A1      11/2021   Buck

FOREIGN PATENT DOCUMENTS

CN          108744320  A     11/2018
CN          109011221  A     12/2018
(Continued)

OTHER PUBLICATIONS

Hiroaki Kumada et al., "Monitoring patient movement with boron neutron capture therapy and motion capture technology", Applied Radiation and Isotopes, published on May 4, 2020, vol. 163, pp. 1-6, published by Elsevier Ltd., Netherlands.*

*Primary Examiner* — Yassin Alata
(74) *Attorney, Agent, or Firm* — CKC & Partners Co., LLC

(57)                ABSTRACT

Tag-guided image positioning method includes: defining a three-dimensional space coordinate system based on tag spatial position information obtained by identifying reference image(s) of a patient's body part disposed with reference tag(s), and position/direction data related to a medical device reference point (MDC)/direction (MDD); estimating a target coordinate in system representing a position of a target point based on three-dimensional medical image of patient's body part marked with target point and reference marker(s) corresponding to position(s) of reference tag(s) and reference coordinate(s) in system representing position(s) of reference tag(s); and outputting a positioning result as a basis for whether patient's body part should be adjusted based on a judgment result indicating whether or not in system a distance between target coordinate and a device coordinate representing a position of MDC and a pointing representing MDD are respectively consistent with a predetermined distance/medical device incident direction in radiotherapy plan for patient's body part.

19 Claims, 12 Drawing Sheets

(52) U.S. Cl.
CPC ..................... *G06T 2200/24* (2013.01); *G06T 2207/30004* (2013.01); *G06T 2207/30204* (2013.01); *G06V 2201/03* (2022.01)

(56) References Cited

FOREIGN PATENT DOCUMENTS

| | | | |
|---|---|---|---|
| EP | 4197592 | A1 | 6/2023 |
| JP | 2017035348 | A | 2/2017 |
| JP | 2022507622 | A | 1/2022 |
| TW | 202222270 | | 6/2022 |
| TW | 202322744 | | 6/2023 |
| TW | 202324450 | | 6/2023 |

* cited by examiner

TU

TTP

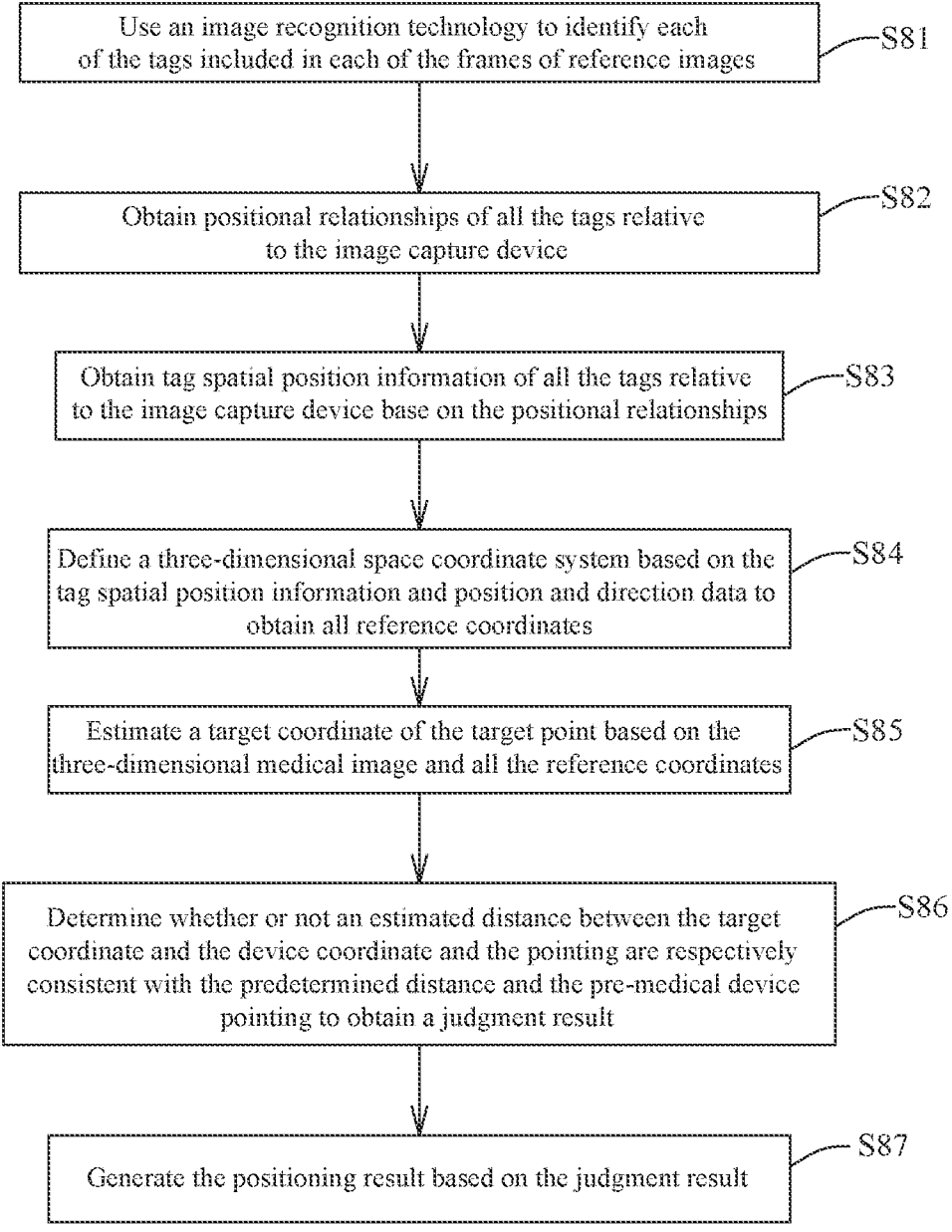

Use an image recognition technology to identify each of the tags included in each of the frames of reference images —S81

Obtain positional relationships of all the tags relative to the image capture device —S82

Obtain tag spatial position information of all the tags relative to the image capture device base on the positional relationships —S83

Define a three-dimensional space coordinate system based on the tag spatial position information and position and direction data to obtain all reference coordinates —S84

Estimate a target coordinate of the target point based on the three-dimensional medical image and all the reference coordinates —S85

Determine whether or not an estimated distance between the target coordinate and the device coordinate and the pointing are respectively consistent with the predetermined distance and the pre-medical device pointing to obtain a judgment result —S86

Generate the positioning result based on the judgment result —S87

Fig. 8

TAG-GUIDED IMAGE POSITIONING METHOD AND SYSTEM

RELATED APPLICATIONS

This application claims priority to Taiwan Application Serial Number 112131972, filed on Aug. 24, 2023, which is herein incorporated by reference in its entirety.

BACKGROUND

Field of Invention

The present disclosure relates to image positioning. More particularly, the present disclosure relates to a tag-guided image positioning method and system.

Description of Related Art

Since uncharged neutrons cannot be turned by using electric fields, like charged particles, such as protons, etc., the current boron neutron capture therapy (hereinafter abbreviated as BNCT) system is limited in physical mechanism, thus making it difficult to realize the design of rotating beam. In addition, for patients receiving BNCT, the irradiation angles and field sizes of the neutron beams received are determined by the evaluation results of the treatment planning systems. Hence, before the BNCT is actually performed, the patient must be positioned through simulation to ensure that the irradiation conditions can be consistent with the irradiation conditions required by the evaluation results.

However, in the current artificial positioning method, a medical physicist usually positions the affected part of the patient, such as a tumor, within the range of the beam by visual estimation. In the positioning process, the positions of the affected part and the feature of the patient's body surface must be marked in the three-dimensional computerized tomography (abbreviated as CT) or positron emission tomography (abbreviated as PET) image first. Then, according to the relative distance between the affected part and the feature in the image, the affected part is positioned by utilizing standard measuring tools and quantifying the distance by visual judgment. Because it is positioned in the three-dimensional space, the final positioning is not completed before the judgments and confirmations are performed many times in different dimensions. This positioning method not only varies in quantitative accuracy during the visual judgment due to the visual acuity of the performer, but the entire positioning process may also even take as long as one hour. As a result, the physical and mental burdens are increased on the patient.

For the foregoing reason, there is a need to provide a fast and high-accuracy image positioning method for BNCT or other radiotherapies, which is one of the subjects to be solved in the related technical field.

SUMMARY

The objective of one embodiment of the present disclosure provides a tag-guided image positioning method and system that can overcome at least one disadvantage of the related art.

One embodiment of the present disclosure provides a tag-guided image positioning method for establishing and/or comparing a relationship between a specific part of a patient and a medical device in a space, and being executed by a computer system, the tag-guided image positioning method including the following steps:

(1) receiving at least one reference image obtained by using an image capture device to capture at least one reference tag corresponding the specific part in position;

(2) using an image recognition technology to identify the at least one reference tag included in the at least one reference image, and obtaining tag spatial position information of the at least one reference tag relative to the image capture device based on a positional relationship of the at least one identified reference tag relative to the image capture device in the space;

(3) calculating a position of the medical device and calculating a position of at least one target point based on a position of the at least one reference tag to obtain a device coordinate and at least one target coordinate; and (4) determining whether or not the at least one target coordinate is adjacent to the device coordinate to obtain a judgment result; and (4-1) generating and outputting a positioning result to serve as a basis for whether the specific part or the medical device should be adjusted or not based on the judgment result.

In the foregoing, step (3) includes:

(3-1) defining a three-dimensional space coordinate system based on the tag spatial position information and position and direction data of the space related to a medical device reference point of the medical device and a medical device direction to obtain at least one reference coordinate representing the position where the at least one reference tag is located, the device coordinate representing a position where the medical device reference point is located, and a pointing representing the medical device direction in the three-dimensional space coordinate system; and (3-2) estimating the at least one target coordinate representing a position where the at least one target point is located in the three-dimensional space coordinate system based on a three-dimensional medical image of the specific part marked with a target marker representing the at least one target point and at least one distinguishable reference marker representing the at least one reference tag corresponding to a position of the specific part and the at least one reference coordinate in the three-dimensional space coordinate system.

In the foregoing, a number of the at least one reference tag is one. When the image capture device is fixed relative to the medical device reference point and the specific part is only attached with the one reference tag, the tag-guided image positioning method further includes the following step before step (3-1): (5) obtaining the position and direction data from an outside, the position and direction data including displacement data of the medical device reference point relative to the image capture device in the space, and direction data of the medical device direction relative to the image capture device in the space.

In the foregoing, when the image capture device is movable relative to the medical device reference point, the specific part is attached with the at least one reference tag, a medical device tag corresponding to the medical device reference point in position and has a unique identification pattern is further disposed in the space where the patient is located, in which:

step (1) includes: the at least one reference image received by the computer system being obtained by capturing the at least one reference tag and the medical device tag by the image capture device; and step (2) includes: the computer system further identifying the medical device tag included in the at least one reference image, and obtaining the position and direction data based on a positional relationship of the identified medical device tag relative to the image capture device in the space.

In the foregoing, the position and direction data includes displacement data of the medical device reference point relative to the image capture device in the space, and direction data of the medical device direction relative to the image capture device in the space.

In the foregoing, step (4) includes: determining whether or not an estimated distance between the at least one target coordinate and the device coordinate and the pointing in the three-dimensional space coordinate system are respectively consistent with a predetermined distance and a pre-medical device pointing included in a predetermined treatment plan to obtain the judgment result; step (4-1) includes: generating and outputting the positioning result to serve as a basis for whether positioning of the specific part should be adjusted or not based on the judgment result.

In the foregoing, step (4) further includes: when the judgment result indicates that the estimated distance is not consistent with the predetermined distance and/or the pointing is not consistent with the pre-medical device pointing, the positioning result generated by the computer system including distance difference data between the estimated distance and the predetermined distance and/or angle difference data between the pointing and the pre-medical device pointing.

In the foregoing, the at least one reference tag is has a unique and exposed identification pattern.

In the foregoing, the image capture device includes at least two cameras. Before step (1) or after step (4), the tag-guided image positioning method further includes the at least two cameras capturing the at least one reference tag or a calibration tag located in the space to calibrate a position of the at least one reference coordinate or a calibration coordinate of the calibration tag in the three-dimensional space coordinate system.

Another embodiment of the present disclosure provides a tag-guided image positioning system for establishing and/or comparing a relationship between a specific part of a patient and a medical device in a space, and the tag-guided image positioning system includes at least one reference tag, an image capture device, a storage module, and a processor. The at least one reference tag is disposed on a position corresponding to the specific part. The image capture device is disposed in a space where the patient is located, and is configured to capture the at least one reference tag to obtain at least one reference image after a positioning process. The storage module is configured to store a tag-guided image positioning application. The processor is configured to execute the tag-guided image positioning application. The tag-guided image positioning application includes the above step (1) to step (4) or step (1) to step (4-1).

In the foregoing, the image capture device is fixedly disposed in the space where the patient is located relative to the medical device reference point; the at least one reference tag is attached to the specific part; and the storage module further stores the position and direction data, the position and direction data comprises displacement data of the medical device reference point relative to the image capture device in the space, and direction data of the medical device direction relative to the image capture device in the space.

In the foregoing, the tag-guided image positioning system further includes a display module. The display module is configured with a graphical interface, and the distance difference data and the angle difference data are displayed by the graphical interface.

The effects of the present disclosure are: due to the use of the reference tags and the medical device tag, the three-dimensional space coordinate system can be easily defined and the device coordinate representing the position where the medical device reference point is located, the pointing representing the beam direction, and the reference coordinates that serve as positioning data for the specific part and representing the positions where the reference tags are located in the three-dimensional space coordinate system are obtained. By using the three-dimensional medical image of the specific part marked with the target marker and the reference markers, the at least one target coordinate representing the position where the at least one target point is located in the three-dimensional space coordinate system can be can easily and relatively accurately estimated. Additionally, the positioning result is generated and output to serve as the basis for whether the positioning of the specific part should be adjusted or not based on the judgment result indicating whether or not in the three-dimensional space coordinate system the estimated distance between the at least one target coordinate and the device coordinate and the pointing representing the beam direction are respectively consistent with the predetermined distance and the predetermined beam incident direction of the predetermined treatment plan for the specific part. In this manner, before or during radiotherapy, the positioning of the specific part can be assisted to be quickly consistent with the positioning of the predetermined treatment plan.

It is to be understood that both the foregoing general description and the following detailed description are by examples, and are intended to provide further explanation of the disclosure as claimed.

BRIEF DESCRIPTION OF THE DRAWINGS

Aspects of the present disclosure are best understood from the following detailed description when read with the accompanying figures. It is noted that, in accordance with the standard practice in the industry, various features are not drawn to scale. In fact, the dimensions of the various features may be arbitrarily increased or reduced for clarity of discussion. The accompanying drawings are included to provide a further understanding of the present disclosure, and are incorporated in and constitute a part of this specification. The drawings illustrate embodiments of the present disclosure and, together with the description, serve to explain the principles of the present disclosure.

5

Figure 5:
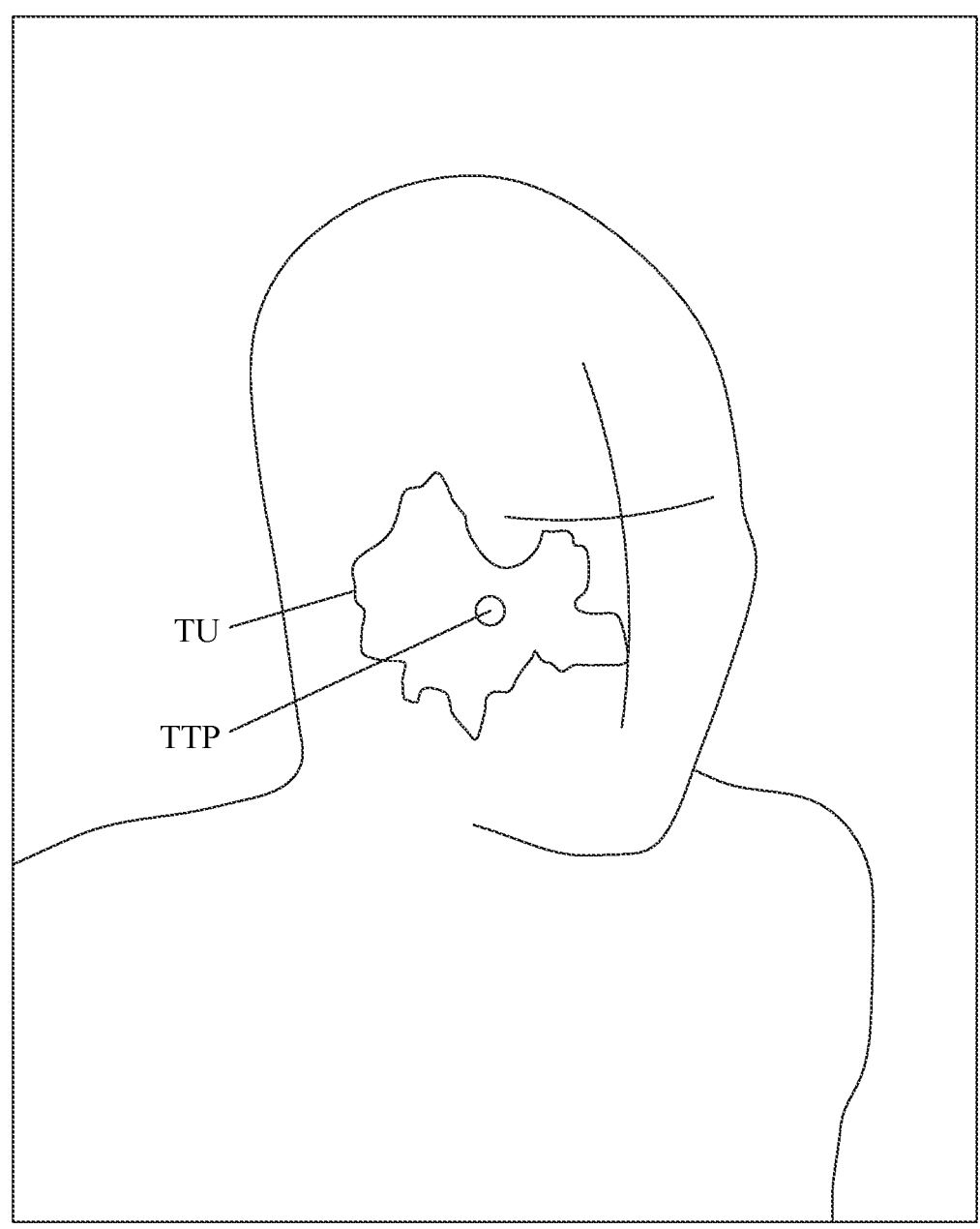

FIG. 5 depicts a three-dimensional CT image of a target point planned by a predetermined treatment plan for a specific part of a patient according to one embodiment of the present disclosure.

Figure 6:
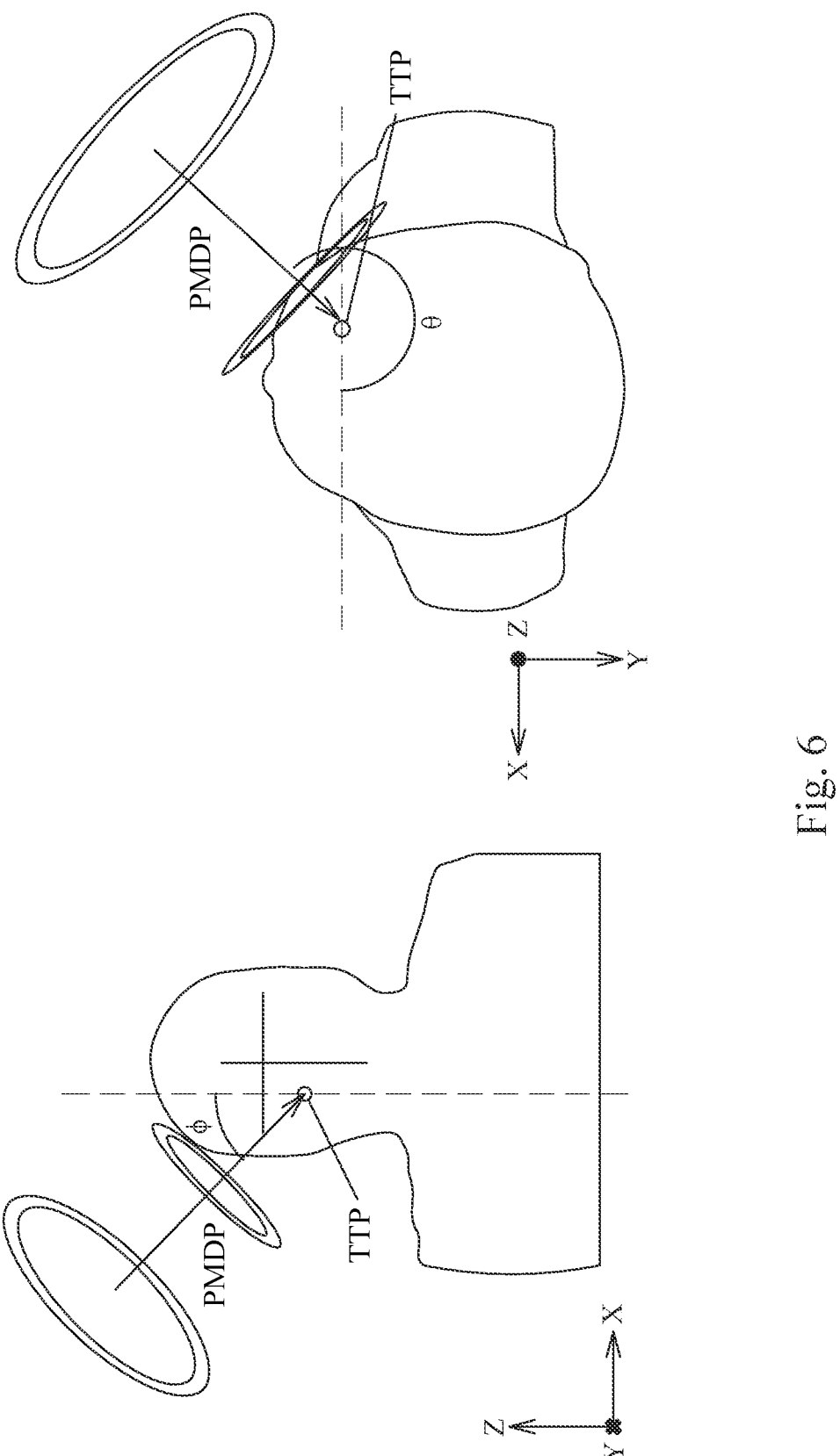

FIG. 6 depicts a schematic diagram of an incident direction of a predetermined medical device planned by a predetermined treatment plan according to one embodiment of the present disclosure.

Figure 7:
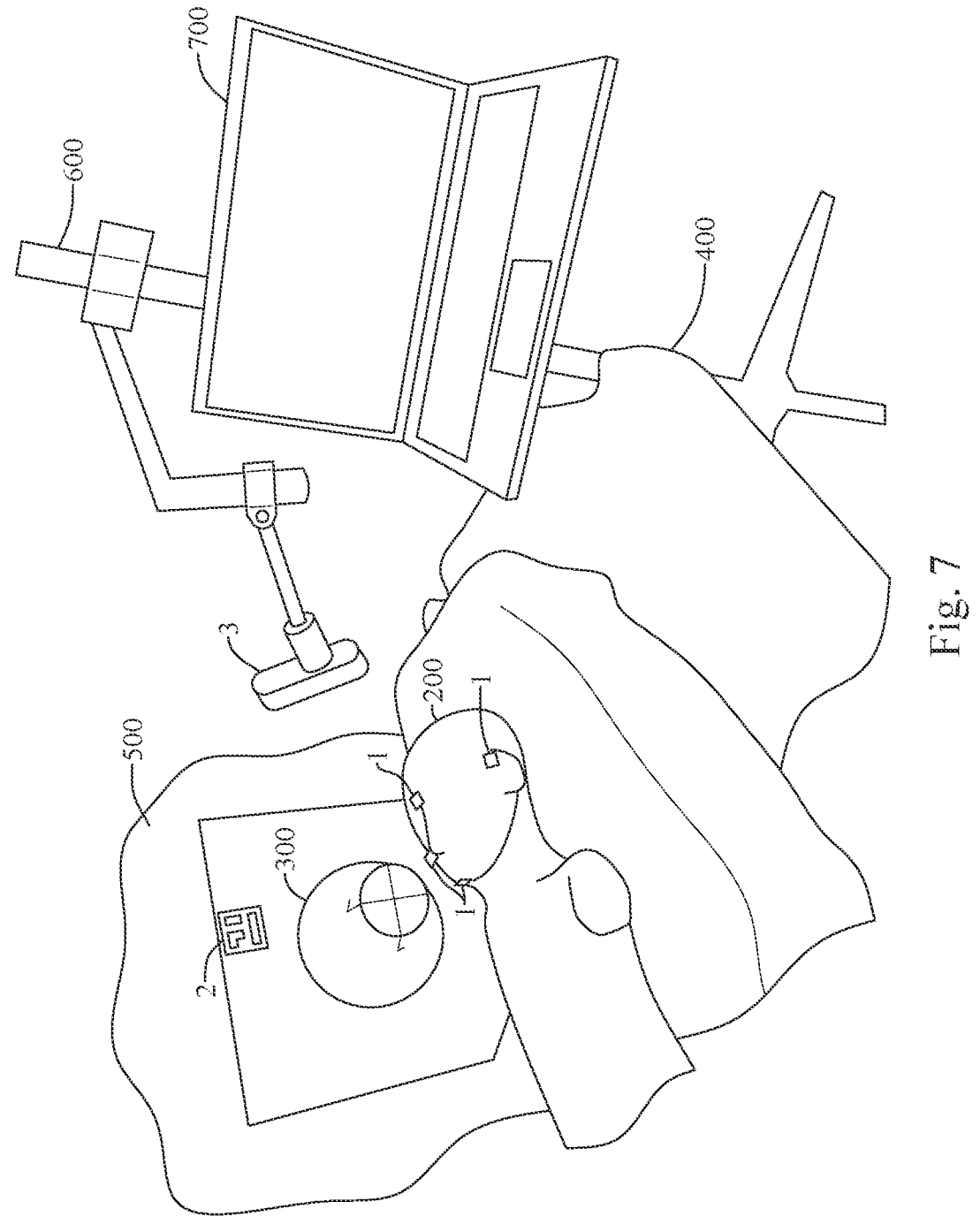

FIG. 7 depicts a schematic diagram of a simulated environment according to one embodiment of the present disclosure.

FIG. 8 depicts a flowchart of a positioning process executed by a processor according to one embodiment of the present disclosure.

Figure 9:
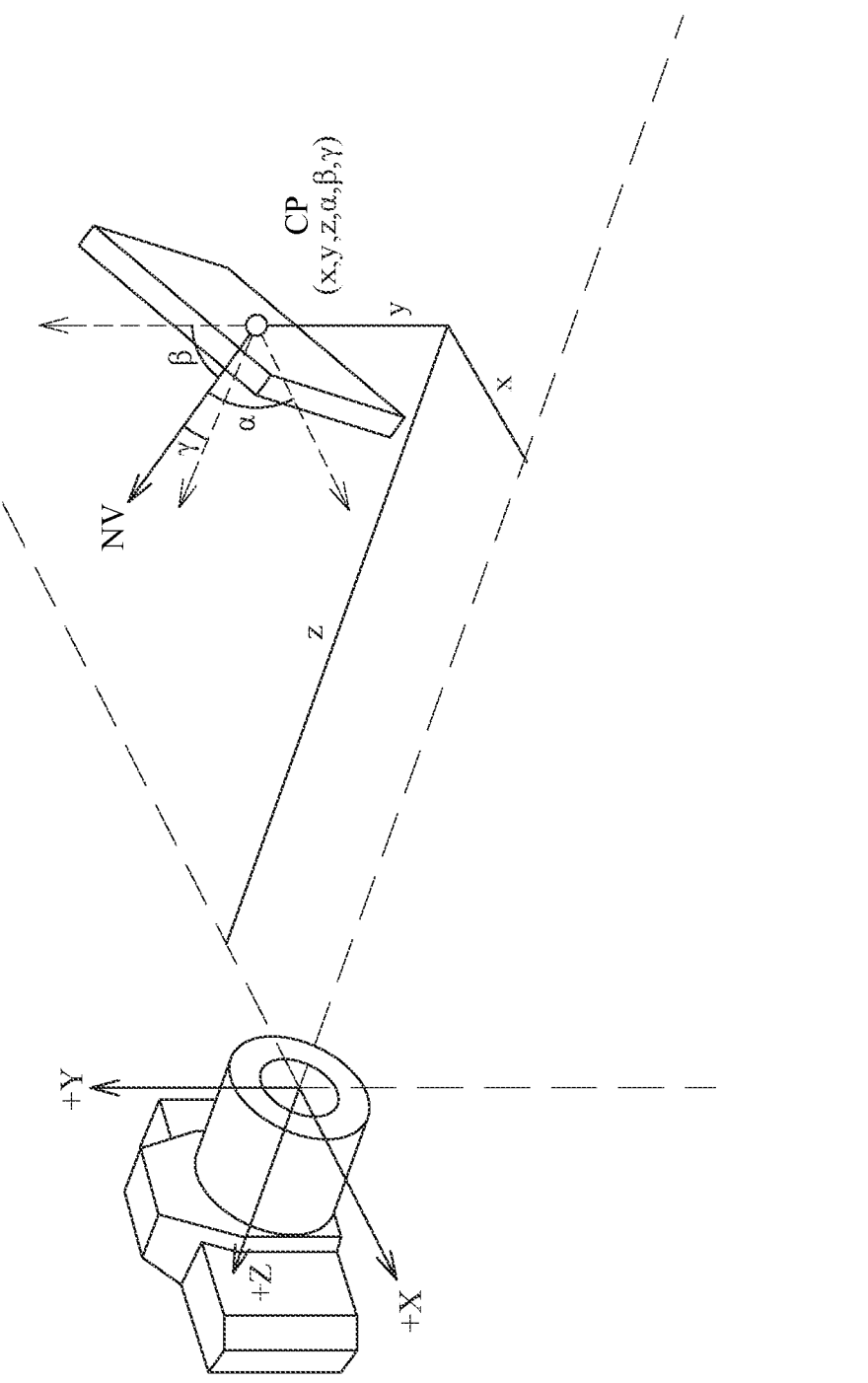

FIG. 9 depicts a schematic diagram of a positional relationship of an identified tag relative to a lens of an image capture device in a space according to one embodiment of the present disclosure.

Figure 10:
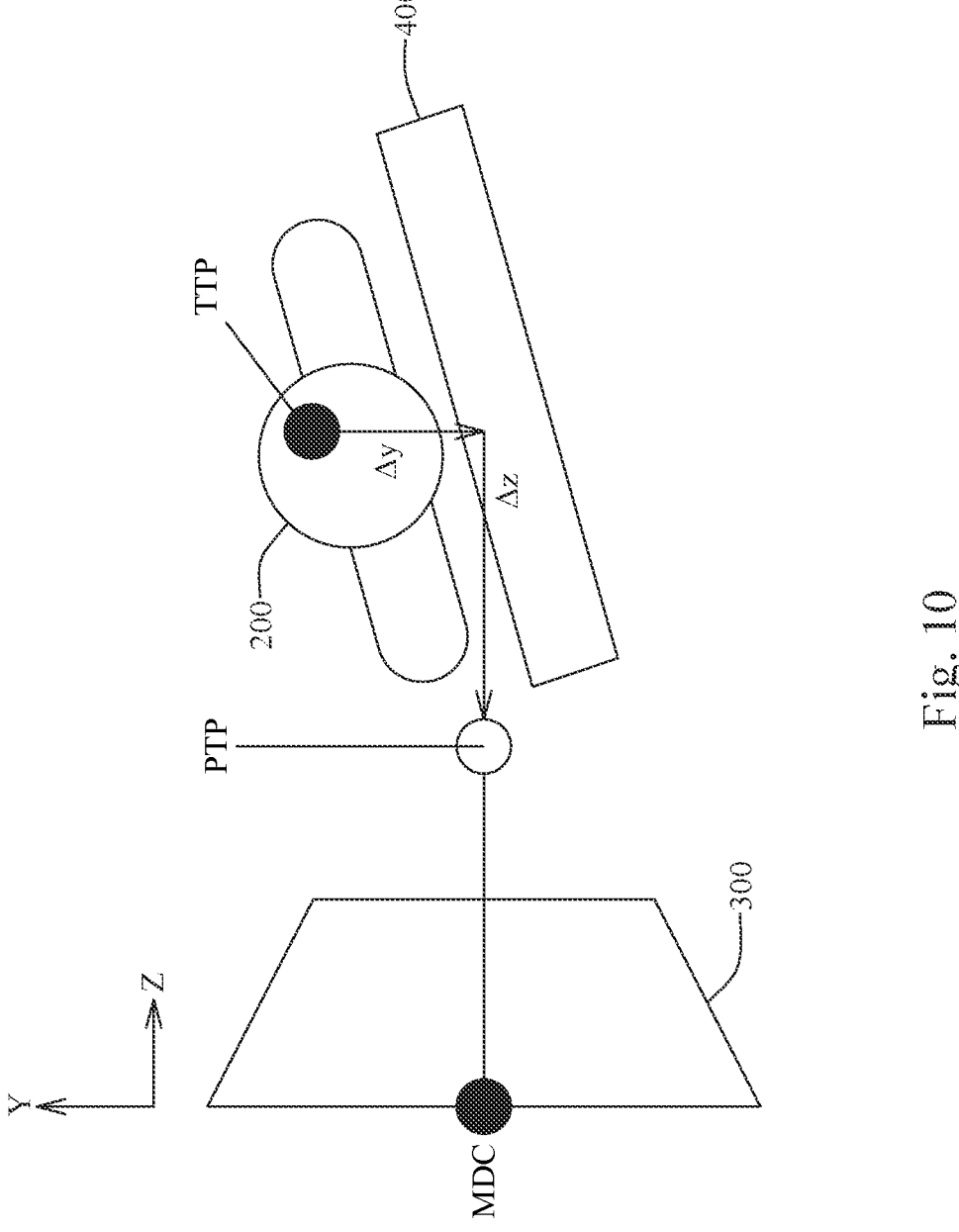

FIG. 10 depicts a schematic diagram of distance differences between a target point and a predetermined treatment point in the Y-axis direction and the Z-axis direction according to one embodiment of the present disclosure.

Figure 11:
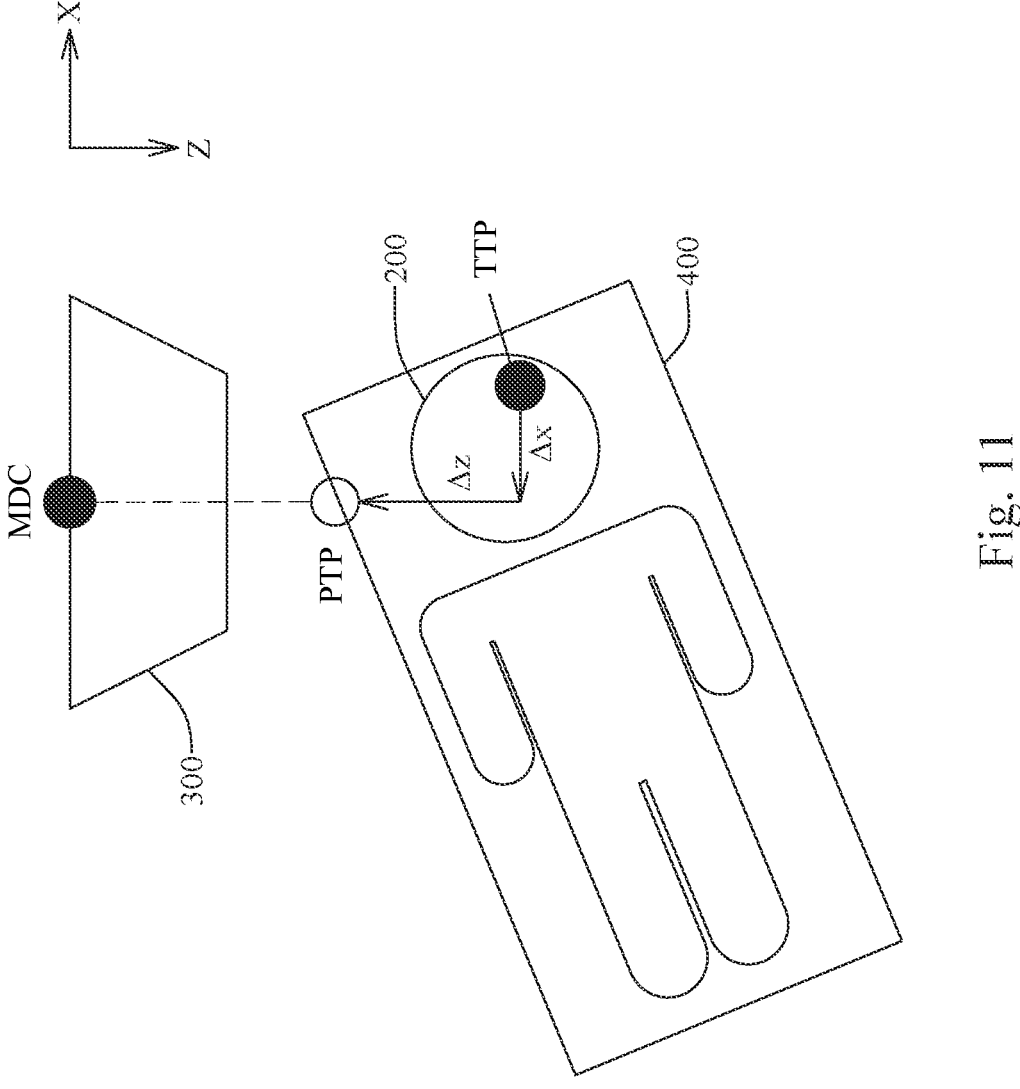

FIG. 11 depicts a schematic diagram of distance differences between the target point and the predetermined treatment point in the X-axis direction and the Z-axis direction according to one embodiment of the present disclosure.

Figure 12:
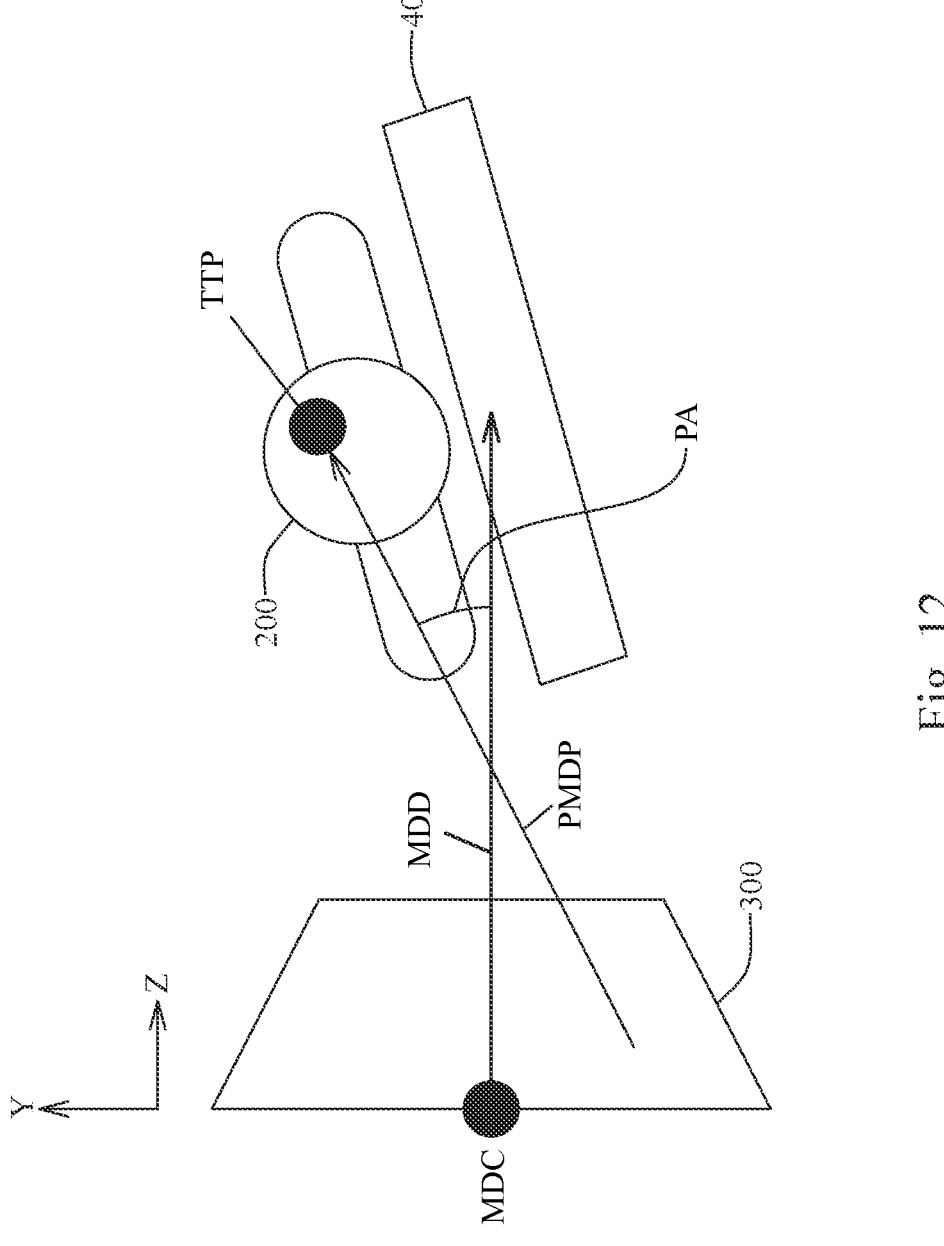

FIG. 12 depicts a schematic diagram of a difference in pitch angle between a medical device direction and a pre-medical device incident direction on the Y-Z plane according to one embodiment of the present disclosure.

Figure 13:
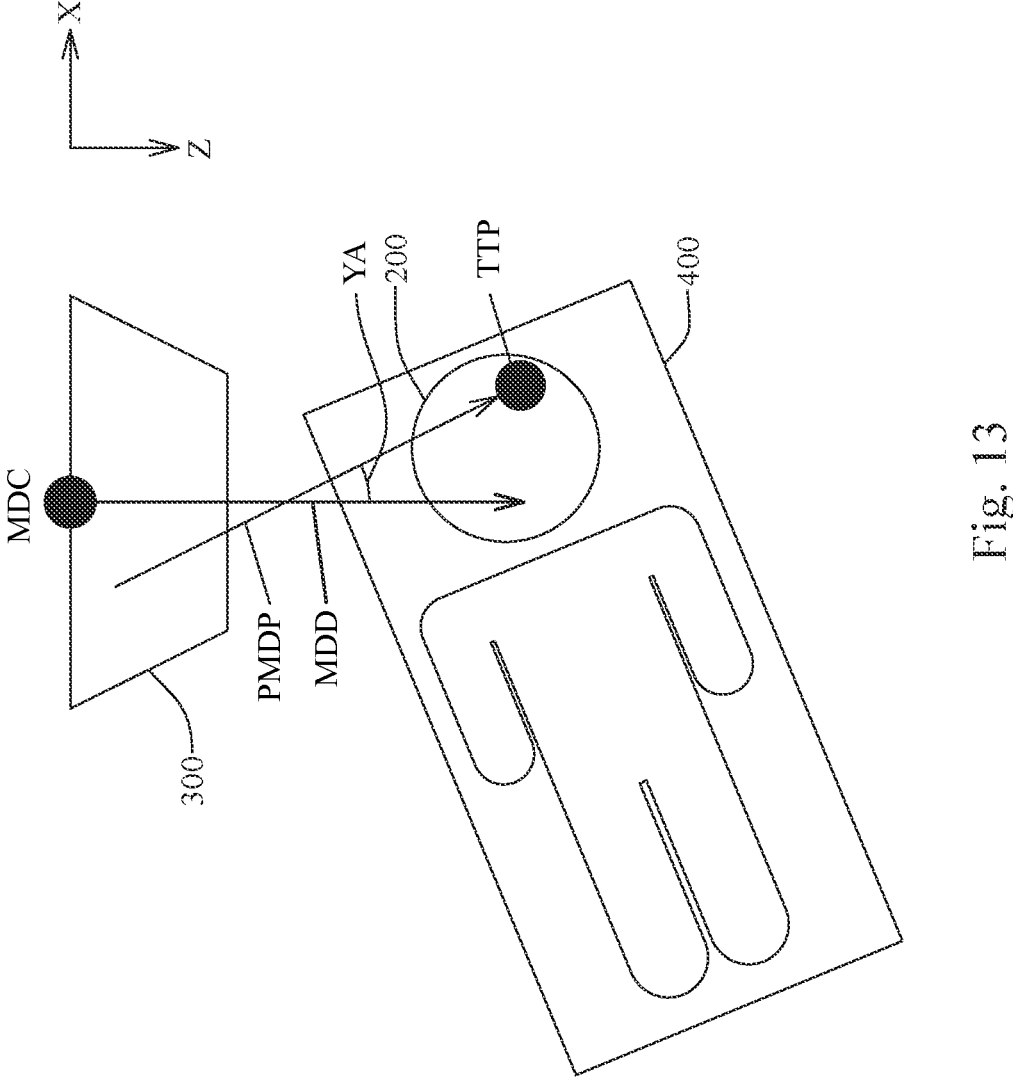

FIG. 13 depicts a schematic diagram of a difference in yaw angle between the medical device direction and the pre-medical device incident direction on the X-Z plane according to one embodiment of the present disclosure.

DESCRIPTION OF THE EMBODIMENTS

To make the contents of the present disclosure more thorough and complete, the following illustrative description is given with regard to the implementation aspects and embodiments of the present disclosure, which is not intended to limit the scope of the present disclosure. The various embodiments disclosed below can be combined or replaced with each other when beneficial, and other embodiment(s) may be added to one embodiment, without further description or illustration. In the following detailed description, for purposes of explanation, numerous specific details are set forth in order to provide a thorough understanding of the disclosed embodiments. It will be apparent, however, that one or more embodiments may be practiced without these specific details.

Further, spatially relative terms, such as "beneath," "below," "lower," "above," "upper" and the like, may be used herein for ease of description to describe one component or feature's relationship to another component(s) or feature(s) as illustrated in the figures. The spatially relative terms are intended to encompass different orientations of the device in use or operation in addition to the orientation depicted in the figures. The device may be otherwise oriented (for example, rotated 90 degrees or at other orientations) and the spatially relative descriptors used herein may likewise be interpreted accordingly.

As used herein, the singular forms "a", "an" and "the" are intended to include the plural forms as well, unless the context clearly indicates otherwise. It will be further understood that the terms "comprises" and/or "comprising", or "includes" and/or "including" or "has" and/or "having" when used in this specification, specify the presence of stated features, regions, integers, steps, operations, elements (devices), and/or components, but do not preclude the presence or addition of one or more other features, regions, integers, steps, operations, elements (devices), components, and/or groups thereof.

Figure 1:
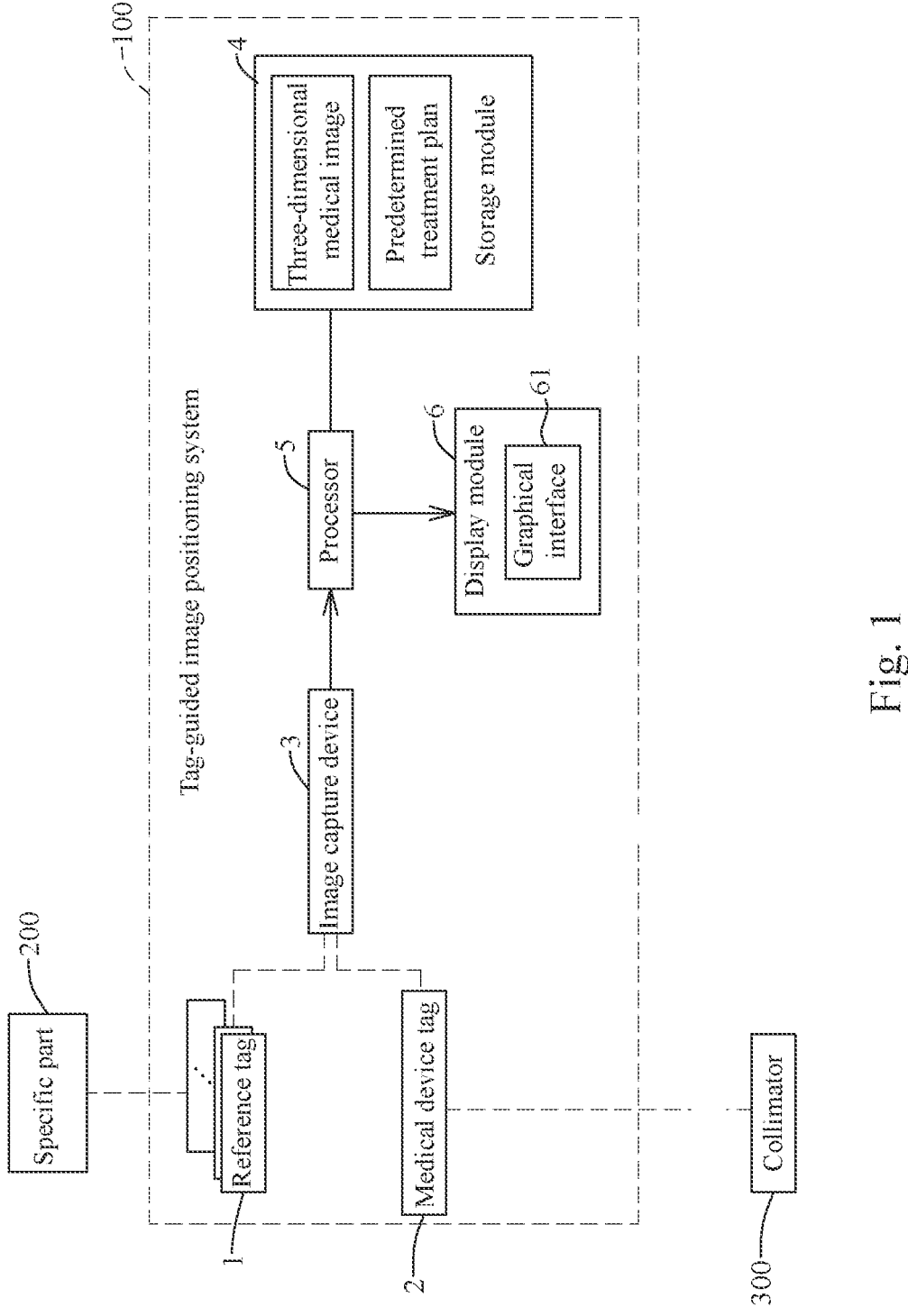
FIG. 1 depicts a block diagram of components of a tag-guided image positioning system according to one embodiment of the present disclosure.

A description is provided with reference to FIG. 1. FIG. 1 depicts a tag-guided image positioning system 100 according to one embodiment of the present disclosure. The tag-guided image positioning system 100 is used for assisting in positioning of a specific part 200 (such as a head) of a patient before or during a radiotherapy, for example but not limited to BNCT, to be consistent with positioning of a predetermined treatment plan for the specific part 200. In the present embodiment, the tag-guided image positioning system 100 includes, for example but not limited to, four reference tags 1, a medical device tag 2, an image capture device 3, a storage module 4, a display module 6, and a processor 5.

Figures 3, 4:
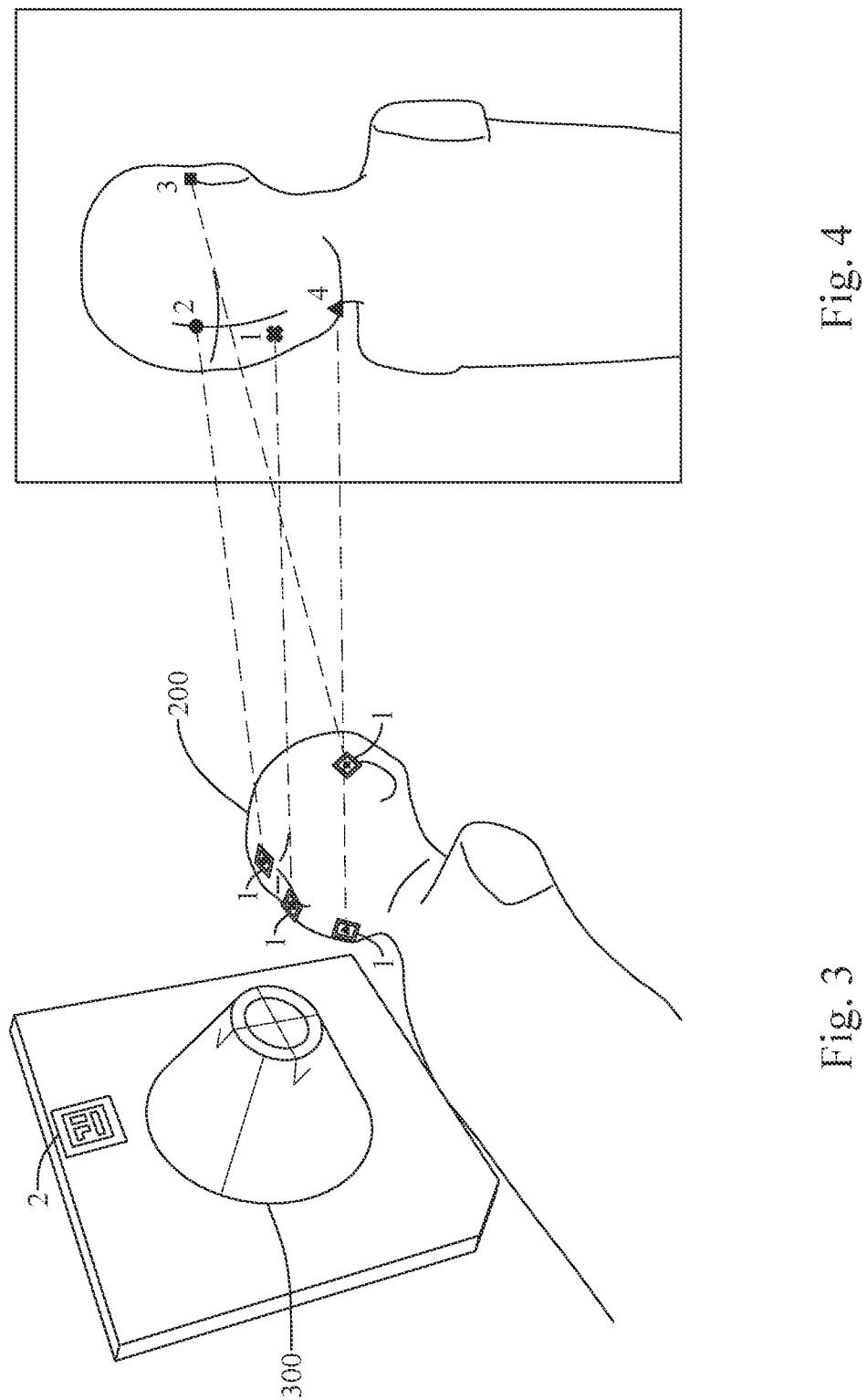
FIG. 3 depicts a schematic diagram of a plurality of reference tags and a medical device tag and their respective attachment positions according to one embodiment of the present disclosure.
FIG. 4 depicts a schematic diagram of a CT image marked with a plurality of reference markers stored by a storage module according to one embodiment of the present disclosure.

In the present embodiment, the reference tags 1 are, for example, directly attached to four different and easily distinguishable positions of the specific part 200 (for example, the position between the eyebrows, the tip of the nose, the tip of the chin, and the top of an ear as shown in FIG. 3), respectively. However, in other embodiments, the reference tags 1 may be attached to an extension (not shown in the figure) that is worn on the specific part 200, such as the head, so that their attachment positions respectively correspond to, for example, the position between the eyebrows, the tip of the nose, the tip of the chin, and the top of the ear.

In the present embodiment, the medical device tag 2 is adapted for being disposed in a space where the patient is located, and has a corresponding relationship in position with a medical device reference point MDC, such as a center (not shown in the figure, also called the beam center) of a beam exit of a BNCT device (not shown in the figure). In addition, each of the reference tags 1 and the medical device tag 2 has a unique identification pattern formed on its exposed surface. For example, each of the reference tags 1 has a different identification pattern to facilitate differentiation, as shown in FIG. 3.

In the present embodiment, the image capture device 3 is movably disposed in the space where the patient is located relative to the medical device reference point MDC, and may include one or more image capture modules (not shown in the figure, such as CCD). Additionally, in each positioning process the image capture device 3 captures multiple frames of reference images including the reference tags 1 and the medical device tag 2.

In the present embodiment, the storage module 4 is configured to store a three-dimensional medical image of the specific part, such as an image attained from CT or magnetic resonance imaging (MRI), and the predetermined treatment plan. The predetermined treatment plan includes, for example, a predetermined distance between the medical device reference point MDC and a target point TTP of the specific part (such as a center point of a tumor TU shown in FIG. 5), and a pre-medical device pointing (PMDP) of a neutron beam incident on the target point TTP (for example, the predetermined beam incident pointing is the direction defined by a polar angle $\phi$ and an azimuth angle $\theta$ shown in FIG. 6). It is noted that, in the present embodiment, the three-dimensional medical image must be marked with a target marker representing the target point TTP and a plurality of distinguishable reference markers respectively representing the attachment positions of the reference tags 1. For example, the CT image shown in FIG. 4 is only marked with four reference markers respectively corresponding to the reference tags 1 in FIG. 3.

Figure 2:
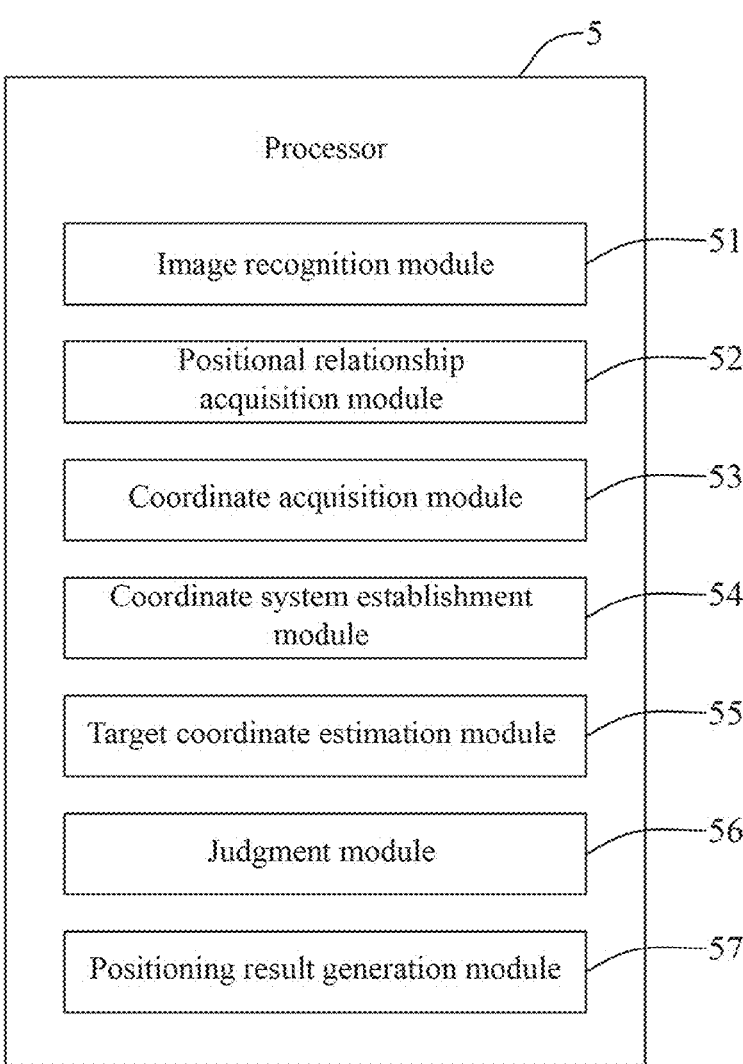
FIG. 2 depicts a block diagram of components of a processor according to one embodiment of the present disclosure.

The processor 5 is electrically connected to the image capture device 3, the storage module 4, and the display module 6, and is configured to execute a positioning process based on the multiple frames of reference images received from the image capture device 3 corresponding to a current positioning process, so as to generate a positioning result corresponding to the current positioning process. In the present embodiment, as shown in FIG. 2, the processor 5 includes, for example, an image recognition module 51, a positional relationship acquisition module 52, a coordinate acquisition module 53, a coordinate system establishment module 54, a target coordinate estimation module 55, a judgment module 56, and a positioning result generation module 57. Their respective operations are described in detail as follows in conjunction with the related description of the positioning process below.

In the present embodiment, the display module 6 is configured with a unique graphical interface 61 and is controlled by the processor 5, so that the display module 6 graphically displays the positioning result from the processor 5 through the graphical interface 61.

In the present embodiment, the tag-guided image positioning system 100 usually can cooperate with a collimator 300 to be used in, for example, a simulated environment shown in FIG. 7. In the example shown in FIG. 7, a dummy human body representing the patient is placed on a treatment bed 400 whose position and angle can be adjusted. The collimator 300 is mounted on a wall 500 symmetrical to a center (not shown in the figure, hereinafter abbreviated as the medical device reference point MDC) of a medical device exit (such as the beam exit) of the BNCT device (not shown in the figure) that penetrates through the wall 500 adjacent to the treatment bed 400 to accurately obtain a medical device direction MDD (or called beam direction) of the neutron beam generated by the BNCT device and emitted from the medical device exit. The four reference tags 1 are respectively attached to positions, for example, between the eyebrows, of the tip of the nose, of the tip of the chin, and at the top of an ear, on the head of the dummy human body. The medical device tag 2 is, for example, attached to a substrate of the collimator 300 at a specific upper position aligned with the medical device reference point MDC. The image capture device 3 is mounted on a movable mounting frame 600, and the storage module 4, the display module 6, and the processor 5 are implemented in a notebook computer 700.

A description is provided with reference to FIG. 1, FIG. 2, and FIG. 8. How the processor 5 executes the positioning process based on the reference images obtained in the current positioning process is described in detail. The positioning process includes the following steps S81-S87.

First, in step S81, the image recognition module 51 of the processor 5 uses an image recognition technology to identify each of the reference tags 1 and the medical device tag 2 included in each of the frames of reference images.

Then, in step S82, the positional relationship acquisition module 52 of the processor 5 obtains positional relationships of the reference tags 1 and the medical device tag 2 relative to the image capture device 3 in the space based on an orientation of the image capture device 3 (lens of the image capture device 3) and images of the reference tags 1 and the medical device tag 2 that are identified. In greater detail, a description is provided with reference to FIG. 9. The positional relationship of any tag of the reference tags 1 and the medical device tag 2 that are identified relative to the image capture device 3 includes, for example, displacements (that is, x, y, z) of a center point CP of the tag relative to the lens of the image capture device 3 respectively in its three axes (that is, X, Y, Z) and inclination angles (that is, $\alpha$, B, Y) of a normal vector NV of the tag respectively relative to the three axes. As a result, the positional relationship corresponding to the tag can be represented by a vector (x, y, z, $\alpha$, $\beta$, $\gamma$). In some embodiments, the tag is a rectangle, and the positional relationship between the image capture device 3 and the tag can be located as long as the image capture device 3 can capture any corner position on the tag (such as the center point, upper left corner, upper right corner, lower left corner, lower right corner, etc.).

After that, in step S83, the coordinate acquisition module 53 of the processor 5 obtains tag spatial position information of the reference tags 1 and the medical device tag 2 relative to the image capture device 3 base on the positional relationships obtained in step S82. In the present embodiment, the tag spatial position information obtained by the coordinate acquisition module 53 includes a plurality of three-dimensional tag coordinates relative to a position where the image capture device 3 is located and respectively representing positions where the reference tags 1 and the medical device tag 2 (the center points of them) are located.

Next, in step S84, the coordinate system establishment module 54 of the processor 5 defines a three-dimensional space coordinate system based on the tag spatial position information and position and direction data of the space related to the medical device reference point MDC and the medical device direction MDD with respect to the BNCT device to obtain a plurality of reference coordinates representing the positions where the reference tags 1 are located, a device coordinate representing a position where the medical device reference point MDC is located, and a pointing representing the medical device direction MDD in the three-dimensional space coordinate system. In greater detail, in the present embodiment, the coordinate system establishment module 54 first, for example, uses the three-dimensional tag coordinate representing the position where the medical device tag 2 is located as a reference point, then obtains two vectors of any two of the reference coordinates representing the positions where the two corresponding reference tags 1 are located respectively relative to the reference point, and calculates the cross product of the two vectors, thus obtaining the positional relationships between the positions where the two corresponding reference tags 1 are located relative to the position where the medical device tag 2 is located. Since the position where the medical device tag 2 is located has a corresponding relationship with the medical device reference point MDC in spatial position, the coordinate system establishment module 54 directly inputs the known positions of the medical device tag 2 and the medical device reference point MDC to define, for example, the three-dimensional space coordinate system that takes the position where the medical device reference point MDC is located as the origin of the coordinate system (that is, device coordinate). In addition to that, the coordinate system establishment module 54 obtains the plurality of reference coordinates respectively representing the positions where the reference tags 1 are located and the pointing representing the medical device direction MDD (for example, a direction perpendicular to and emitting from the wall 500 in FIG. 7) through the three-dimensional space coordinate system.

It is noted that, since the image capture device 3 in the present embodiment is movable, the position where the medical device reference point MDC is located needs to be further determined based on its corresponding relationship with the position where the medical device tag 2 is located and through the obtained position where the medical device tag 2 is located. However, in other embodiments, especially when the image capture device 3 is fixedly disposed and its positional relationship with the medical device reference point MDC is known, the above medical device tag 2 can be omitted, and the storage module 4 only needs to pre-store position and direction data. In other words, the position and direction data includes displacement data of the medical device reference point MDC relative to the image capture device 3 in the space, and direction data of the medical device direction MDD relative to the image capture device 3 in the space. Therefore, the image recognition module 51 only needs to identify the reference tags 1 in step S81, the positional relationship acquisition module 52 only needs to obtain the positional relationships of the reference tags 1 relative to the image capture device 3 in step S82, the coordinate acquisition module 53 obtains the three-dimensional tag coordinate representing the position where each of the reference tags 1 is located in step S83, and the coordinate system establishment module 54 can directly define the three-dimensional space coordinate system that takes the medical device reference point MDC as the origin of the coordinate system and obtain the plurality of reference coordinates representing the positions where the reference tags 1 are located and the pointing representing the medical device direction MDD based on all the obtained three-dimensional tag coordinates representing the positions where the reference tags 1 are located and the position and direction data stored in the storage module 4 in step S84.

Then, in step S85, the target coordinate estimation module 55 of the processor 5 estimates a target coordinate in the three-dimensional space coordinate system representing a position where the target point is located based on the three-dimensional medical image stored in the storage module 4 and the reference coordinates in the three-dimensional space coordinate system. In greater detail, the target coordinate estimation module 55 can obtain a marker position relationship between the target marker and each of the reference markers based on the target marker representing the target point and a plurality of three-dimensional marker coordinates of the reference markers respectively representing the attachment positions of the reference tags 1 in a medical image coordinate system of the three-dimensional medical image, and estimate the target coordinate in the three-dimensional space coordinate system based on the obtained marker position relationships and the reference coordinates in the three-dimensional space coordinate system.

After that, in step S86, the judgment module 56 of the processor 5 determines whether or not an estimated distance between the target coordinate and the device coordinate and the pointing in the three-dimensional space coordinate system are respectively consistent with the predetermined distance and the pre-medical device pointing PMDP stored in the storage module 4 to generate a judgment result. In the present embodiment, the judgment result may indicate that the estimated distance and the pointing are respectively consistent with the predetermined distance and the pre-medical device pointing PMDP, or indicate that the estimated distance is not consistent with the predetermined distance and/or the pointing is not consistent with the pre-medical device pointing PMDP.

Finally, in step S87, the positioning result generation module 57 of the processor 5 generates the positioning result based on the judgment result, and outputs the positioning result to the display module 6 for the display module 6 to display the positioning result through the graphical interface 61 as a basis for whether positioning of the specific part should be adjusted or not. In greater detail, when the judgment result indicates that the estimated distance is not consistent with the predetermined distance and/or the pointing is not consistent with the pre-medical device pointing PMDP, the positioning result generated by the positioning result generation module 57 includes distance difference data between the estimated distance and the predetermined distance and/or angle difference data between the pointing and the pre-medical device pointing PMDP. For example, a description is provided with reference to FIG. 10 and FIG. 11. The distance difference data may include, for example, a distance difference Δy (see FIG. 10) between the target point TTP and a predetermined treatment point PTP in the Y-axis direction (vertical direction), a distance difference Δz (see FIG. 10 and FIG. 11) between the target point TTP and the predetermined treatment point PTP in the Z-axis direction (the medical device emitting direction), and a distance difference Δx (see FIG. 11) between the target point TTP and the predetermined treatment point PTP in the X-axis direction (horizontal direction). In addition, a description is provided with reference to FIG. 12 and FIG. 13. The angle difference data may include, for example, a difference in pitch angle PA between the medical device direction MDD and the pre-medical device pointing PMDP on the Y-Z plane, and a difference in yaw angle YA between the medical device direction MDD and the pre-medical device pointing PMDP on the X-Z plane.

According to the above example, since the positioning result includes the three-dimensional distance differences (that is, Δx, Δy, Δz) and the difference in pitch angle and the difference in yaw angle (that is, PA, YA), the graphical interface 61 of the display module 6 can be appropriately planned so that the graphical interface 61 can properly display the positioning result. Not only are the three-dimensional distance differences, the difference in pitch angle, and the difference in yaw angle are presented in the form of numerical values, but the positioning result is also presented in specific patterns and corresponding numbers matched with each other, so as to more clearly show the difference between the positioning result and the positioning of the predetermined treatment plan.

As a result, through the positioning result displayed by the graphical interface 61, if the displayed three-dimensional distance differences (that is, Δx, Δy, Δz), difference in pitch angle, and difference in yaw angle (that is, PA, YA) are all zero, it means that the positioning of the specific part 200 is consistent with the positioning of the predetermined treatment plan. Otherwise, relevant personnel can control the treatment bed 400 shown in FIG. 7 according to the content of the positioning result to adjust the specific part 200. After the positioning of the specific part 200 is adjusted, the processor 5 executes the positioning process again based on the multiple frames of reference images obtained by capturing the reference tags 1 and the medical device tag 2 again by the image capture device 3. By repeatedly executing the positioning process, the positioning consistent with the predetermined treatment plan can be achieved relatively accurately and quickly.

In summary, due to the use of the reference tags 1 and the medical device tag 2, the processor 5 can easily define the three-dimensional space coordinate system and obtain the device coordinate representing the position where the medical device reference point MDC is located, the pointing representing the medical device direction MDD, and the reference coordinates that serve as positioning data for the specific part and representing the positions where the reference tags are located in the three-dimensional space coordinate system. The processor 5 can easily and relatively accurately estimate the target coordinate representing the position where the target point TTP is located in the three-dimensional space coordinate system by using the three-dimensional medical image of the specific part stored in the storage module 4 and marked with the target marker and the reference markers. Additionally, the processor 5 generates and outputs the positioning result to serve as the basis for whether the positioning of the specific part should be adjusted or not based on the judgment result indicating whether or not in the three-dimensional space coordinate system the estimated distance between the target coordinate and the device coordinate and the pointing representing the medical device direction MDD are respectively consistent with the predetermined distance and the pre-medical device pointing PMDP of the predetermined treatment plan for the specific part. In this manner, before or during radiotherapy, the positioning of the specific part can be assisted to be quickly consistent with the positioning of the predetermined treatment plan. As a result, the tag-guided image positioning system 100 of the present disclosure can indeed achieve the objective of the present disclosure.

In some embodiments, the present disclosure provides a calibration method. The calibration method may be performed before or after executing the positioning method. The image capture device includes at least two cameras, and the at least two cameras capture at least one of the reference tags 1 or a calibration tag located in the space to calibrate a position of at least one reference coordinate or a calibration coordinate of the calibration tag in the three-dimensional space coordinate system. In greater detail, when there are multiple cameras (for example, two cameras), the calibration tag can be used for calibration. The calibration tag may be any one of the above tags (for example, the reference tags 1 or the medical device tag 2). As long as the multiple cameras capture the same tag, the tag can be used for calibration.

In some embodiments, in addition to the above positioning application in boron neutron therapy, the present disclosure can also be applied to positioning applications in other radiotherapies.

In some embodiments, the present disclosure may also mark the medical device tag 2 on surgical instruments. As compared with BNTC, the difference lies in that whether or not in the three-dimensional space coordinate system the target coordinate on the patient is adjacent to the device coordinate of the medical device tag 2 is determined. In other words, there is no necessity to determine whether the predetermined distance and pre-medical device pointing PMDP are met or not. In greater detail, the medical device tag 2 is disposed on a scalpel, and the positioning can be performed as long as a relative position between the medical device tag 2 on the scalpel and the target coordinate (such as the tumor position) on the patient is located. The positioning can be performed continuously and dynamically to master and adjust the positions of surgical instruments and tumor at any time.

In some embodiments, the present disclosure may also mark the medical device tag 2 on a biological sampling syringe. As compared with BNTC, the difference lies in that whether or not in the three-dimensional space coordinate system the target coordinate on the patient is adjacent to the device coordinate of the medical device tag 2 is determined. In other words, there is no necessity to determine whether the predetermined distance and pre-medical device pointing PMDP are met or not. In greater detail, the medical device tag 2 is disposed on the syringe, and the positioning can be performed as long as a relative position between the medical device tag 2 disposed on the syringe and the target coordinate (such as the tumor position) on the patient is located.

In some embodiments, the present disclosure may also mark the medical device tag 2 on catheters in minimally invasive surgery. As compared with BNTC, the difference lies in that whether or not in the three-dimensional space coordinate system the target coordinate on the patient is adjacent to the device coordinate of the medical device tag 2 is determined. In other words, there is no necessity to determine whether the predetermined distance and pre-medical device pointing PMDP are met or not. In greater detail, the medical device tag 2 is disposed on the catheter, and the positioning can be performed as long as a relative position between the medical device tag 2 disposed on the catheter and the target coordinate (such as the tumor position) on the patient is located.

Although the present disclosure has been described in considerable detail with reference to certain embodiments thereof, other embodiments are possible. Therefore, the spirit and scope of the appended claims should not be limited to the description of the embodiments contained herein.

What is claimed is:

1. A tag-guided image positioning method for establishing and/or comparing a relationship between a specific part of a patient and a medical device in a space, and being executed by a computer system, the tag-guided image positioning method comprising the following steps:

(1) receiving at least one reference image obtained by using an image capture device to capture at least one reference tag corresponding the specific part in position;

(2) using an image recognition technology to identify the at least one reference tag comprised in the at least one reference image, and obtaining tag spatial position information of the at least one reference tag relative to the image capture device based on a positional relationship of the at least one identified reference tag relative to the image capture device in the space;

(3) calculating a position of the medical device and calculating a position of at least one target point based on a position of the at least one reference tag to obtain a device coordinate and at least one target coordinate; and (4) determining whether or not the at least one target coordinate is adjacent to the device coordinate to obtain a judgment result.

2. The tag-guided image positioning method of claim 1, wherein step (3) comprises:

(3-1) defining a three-dimensional space coordinate system based on the tag spatial position information and position and direction data of the space related to a medical device reference point of the medical device and a medical device direction to obtain at least one reference coordinate representing the position where the at least one reference tag is located, the device coordinate representing a position where the medical device reference point is located, and a pointing representing the medical device direction in the three-dimensional space coordinate system; and (3-2) estimating the at least one target coordinate representing a position where the at least one target point is located in the three-dimensional space coordinate system based on a three-dimensional medical image of the specific part marked with a target marker representing the at least one target point and at least one distinguishable reference marker representing the at least one reference tag corresponding to a position of the specific part and the at least one reference coordinate in the three-dimensional space coordinate system.

3. The tag-guided image positioning method of claim 2, wherein a number of the at least one reference tag is one, when the image capture device is fixed relative to the medical device reference point and the specific part is only attached with the one reference tag, the tag-guided image positioning method further comprises the following step before step (3-1): (5) obtaining the position and direction data from an outside, the position and direction data comprising displacement data of the medical device reference point relative to the image capture device in the space, and direction data of the medical device direction relative to the image capture device in the space.

4. The tag-guided image positioning method of claim 2, wherein when the image capture device is movable relative to the medical device reference point, the specific part is attached with the at least one reference tag, a medical device tag corresponding to the medical device reference point in position and has a unique identification pattern is further disposed in the space where the patient is located, wherein:
   step (1) comprises: the at least one reference image received by the computer system being obtained by capturing the at least one reference tag and the medical device tag by the image capture device; and
   step (2) comprises: the computer system further identifying the medical device tag comprised in the at least one reference image, and obtaining the position and direction data based on a positional relationship of the identified medical device tag relative to the image capture device in the space.

5. The tag-guided image positioning method of claim 4, wherein the position and direction data comprises displacement data of the medical device reference point relative to the image capture device in the space, and direction data of the medical device direction relative to the image capture device in the space.

6. The tag-guided image positioning method of claim 2, wherein:
   step (4) comprises: determining whether or not an estimated distance between the at least one target coordinate and the device coordinate and the pointing in the three-dimensional space coordinate system are respectively consistent with a predetermined distance and a pre-medical device pointing comprised in a predetermined treatment plan to obtain the judgment result.

7. The tag-guided image positioning method of claim 6, wherein step (4) further comprises: when the judgment result indicates that the estimated distance is not consistent with the predetermined distance and/or the pointing is not consistent with the pre-medical device pointing, a positioning result generated by the computer system comprising distance difference data between the estimated distance and the predetermined distance and/or angle difference data between the pointing and the pre-medical device pointing.

8. The tag-guided image positioning method of claim 1, wherein the at least one reference tag has a unique and exposed identification pattern.

9. The tag-guided image positioning method of claim 2, wherein the image capture device comprises at least two cameras;
   wherein before step (1) or after step (4), the tag-guided image positioning method further comprises the at least two cameras capturing the at least one reference tag or a calibration tag located in the space to calibrate a position of the at least one reference coordinate or a calibration coordinate of the calibration tag in the three-dimensional space coordinate system.

10. A tag-guided image positioning system for establishing and/or comparing a relationship between a specific part of a patient and a medical device in a space, and the tag-guided image positioning system comprising:
   at least one reference tag disposed on a position corresponding to the specific part;
   an image capture device disposed in the space where the patient is located, and being configured to capture the at least one reference tag to obtain at least one reference image after a positioning process;
   a storage module configured to store a tag-guided image positioning application; and
   a processor configured to execute the tag-guided image positioning application, the tag-guided image positioning application comprising the following steps:
      (1) receiving the at least one reference image obtained by using the image capture device to capture the at least one reference tag corresponding the specific part in position;
      (2) using an image recognition technology to identify the at least one reference tag comprised in the at least one reference image, and obtaining tag spatial position information of the at least one reference tag relative to the image capture device based on a positional relationship of the at least one identified reference tag relative to the image capture device in the space;
      (3) calculating a position of the medical device and calculating a position of at least one target point based on a position of the at least one reference tag to obtain a device coordinate and at least one target coordinate; and
      (4) determining whether or not the at least one target coordinate is adjacent to the device coordinate to obtain a judgment result.

11. The tag-guided image positioning system of claim 10, wherein step (3) further comprises:
   (3-1) defining a three-dimensional space coordinate system based on the tag spatial position information and position and direction data of the space related to a medical device reference point of the medical device and a medical device direction to obtain at least one reference coordinate representing the position where the at least one reference tag is located, the device coordinate representing a position where the medical device reference point is located, and a pointing representing the medical device direction in the three-dimensional space coordinate system; and
   (3-2) estimating the at least one target coordinate representing a position where the at least one target point is located in the three-dimensional space coordinate system based on a three-dimensional medical image of the specific part marked with a target marker representing the at least one target point and at least one distinguishable reference marker representing the at least one reference tag corresponding to a position of the specific part and the at least one reference coordinate in the three-dimensional space coordinate system.

12. The tag-guided image positioning system of claim 11, wherein:
   the image capture device is fixedly disposed in the space where the patient is located relative to the medical device reference point;

the at least one reference tag is attached to the specific part; and the storage module further stores the position and direction data, the position and direction data comprises displacement data of the medical device reference point relative to the image capture device in the space, and direction data of the medical device direction relative to the image capture device in the space.

13. The tag-guided image positioning system of claim 11, further comprising a medical device tag disposed in the space where the patient is located and corresponding to the medical device reference point in position, the medical device tag has a unique identification pattern, wherein:

step (1) comprises: the at least one reference image received by the processor being obtained by capturing the at least one reference tag and the medical device tag by the image capture device; and step (2) comprises: the processor further identifying the medical device tag comprised in the at least one reference image, and further obtaining the position and direction data based on a positional relationship of the identified medical device tag relative to the image capture device in the space.

14. The tag-guided image positioning system of claim 13, wherein the position and direction data comprises displacement data of the medical device reference point relative to the image capture device in the space, and direction data of the medical device direction relative to the image capture device in the space.

15. The tag-guided image positioning system of claim 11, wherein:

step (4) comprises: determining whether or not an estimated distance between the at least one target coordinate and the device coordinate and the pointing in the three-dimensional space coordinate system are respectively consistent with a predetermined distance and a pre-medical device pointing comprised in a predetermined treatment plan to obtain the judgment result.

16. The tag-guided image positioning system of claim 15, wherein step (4) further comprises: when the judgment result indicates that the estimated distance is not consistent with the predetermined distance and/or the pointing is not consistent with the pre-medical device pointing, a positioning result generated by the processor comprising distance difference data between the estimated distance and the predetermined distance and/or angle difference data between the pointing and the pre-medical device pointing.

17. The tag-guided image positioning system of claim 16, further comprising a display module, the display module being configured with a graphical interface, and the distance difference data and the angle difference data being displayed by the graphical interface.

18. The tag-guided image positioning system of claim 10, wherein the at least one reference tag has a unique and exposed identification pattern.

19. The tag-guided image positioning system of claim 11, wherein the image capture device comprises at least two cameras;

wherein before step (1) or after step (4), the tag-guided image positioning application further comprises following step: the at least two cameras capturing the at least one reference tag or a calibration tag located in the space to calibrate a position of the at least one reference coordinate or a calibration coordinate of the calibration tag in the three-dimensional space coordinate system.

\* \* \* \* \*